United States Patent [19]

Michel et al.

[11] Patent Number: 4,956,508
[45] Date of Patent: Sep. 11, 1990

[54] PROCESS FOR PREPARING POLYALKYL PERYLENES, PERYLENES OBTAINED BY THIS PROCESS, AND ORGANIC MATERIALS WITH ESR PROPERTIES DERIVED FROM THE SAME

[75] Inventors: Philippe Michel; Alexandre Moradpour, both of Paris; Paul Penven, Orsay, all of France

[73] Assignee: Thomson-CSF, Paris, France

[21] Appl. No.: 307,550

[22] Filed: Feb. 8, 1989

[30] Foreign Application Priority Data

Feb. 12, 1988 [FR] France ................ 88 01682

[51] Int. Cl.$^5$ ............................ C07C 13/465
[52] U.S. Cl. ....................... 585/26; 585/411; 585/422
[58] Field of Search .......................... 585/26

[56] References Cited

U.S. PATENT DOCUMENTS 3,132,187  5/1964  Turetzky .

FOREIGN PATENT DOCUMENTS 469553 11/1928 Fed. Rep. of Germany .
638002 10/1936 Fed. Rep. of Germany .
2640471  3/1977 Fed. Rep. of Germany .

OTHER PUBLICATIONS

"An Electron Spin Resonance Investigation of the Products of the Friedel–Crafts Reaction of Sulfur Dioxide with Methylnaphthalenes", Bakker et al., J. Chem. Soc. (PT II) 1986; 1735–1741.
"Fluorescence and Absorption Properties of Perylenyl and Perylenoyl Probe Molecules in Solvents and Liquid Crystals", Johansson et al., J. Am. Chem. Soc. (1987) 109: 7374–7381.
Chemical Abstracts vol. 69, No. 19, Nov. 4, 1968, p. 7104; S. P. Solodovnikov, et al. Abstract #76168.
Beilsteins Handbuch der Organischen Chemie, vol. 4, Supp. III, 1965, p. E III 5/2538.

Primary Examiner—H. M. S. Sneed
Assistant Examiner—J. Saba
Attorney, Agent, or Firm—Oblon, Spivak, McClelland, Maier & Neustadt

[57] ABSTRACT

The invention relates to a process for preparing a polyalkyl perylene which consists in subjecting the corresponding polyalkyl 1,1'-dinaphthalene derivative to a cyclodehydrogenation reaction, by means of an alkali metal. It also relates to the polyalkyl perylene obtained, and to the organic material derived therefrom exhibiting an electron spin resonance spectrum.

1 Claim, 1 Drawing Sheet

FIG_1
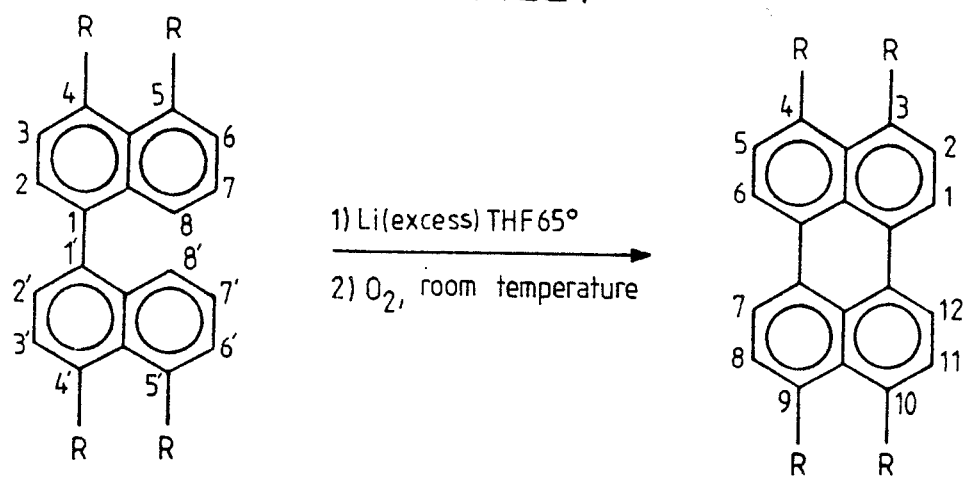
FIG_2
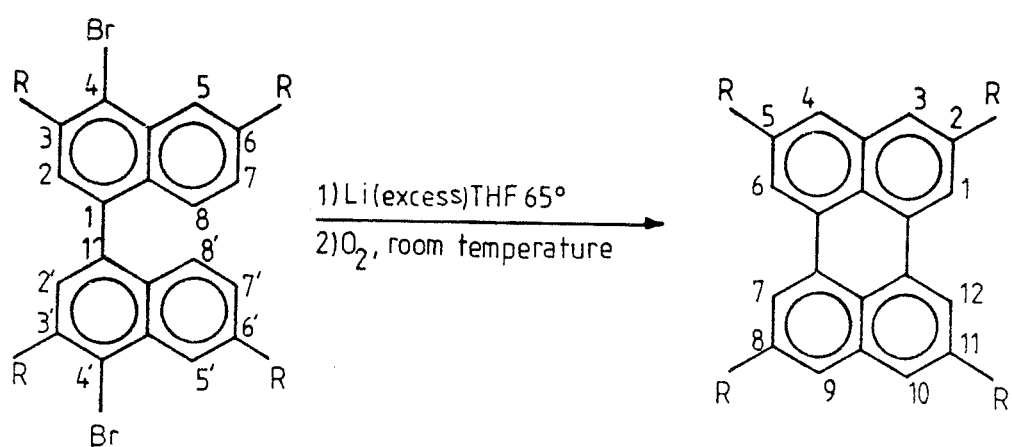

PROCESS FOR PREPARING POLYALKYL PERYLENES, PERYLENES OBTAINED BY THIS PROCESS, AND ORGANIC MATERIALS WITH ESR PROPERTIES DERIVED FROM THE SAME

BACKGROUND OF THE INVENTION (1) Field of the Invention

The present invention relates to a new process for preparing polyalkyl perylenes. It also relates to new products obtained by this process, i.e. polyalkyl perylenes and organic materials, which are derived therefrom and which possess remarkable electron spin resonance properties.

(2) Description of the Prior Art

The radical cation salts derived from certain condensed polyaromatic hydrocarbons, such as fluoranthene (FA) and perylene (PY), have remarkable electron spin resonance (ESR) properties. For example, a remarkably narrow ESR signal was observed at room temperature with $(FA)_2,PF_6$.

This material has a field absorption signal derivative peak-peak width which amounts to a mere 15 milligauss. This signal is thus virtually 100 times narrower than the ESR signal of diphenylpicrylhydrazyl (DPPH), generally used as field marker in ESR. Although the absence of heteroatoms in these materials can be favorable to the narrowing of the ESR lines, on the other hand, this factor leads to a certain thermal instability. Thus for example, salts prepared from naphthalene are only stable beneath $-40°$ C., while the width of the corresponding ESR line is the narrowest (4 milligauss), amongst this whole series of materials.

The remarkable narrowness of these electron spin resonance lines should enable these materials to be used for realizing highly sensitive magnetometers, provided their thermal stability in time, presently quite inadequate, was significantly improved.

To remedy these deficiencies, the invention proposes new materials prepared from polyalkyl perylenes, which can replace advantageously prior art organic materials, such as those derived from fluoranthene, for the realization of ESR magnetic probes. To synthetize these new products, it was necessary to resort to a novel preparation process. This process makes use of a cyclodehydrogenation reaction of the corresponding 1,1'-dinaphthalene derivatives, initiated by metallic lithium. Compared with prior art processes, this invention offers the advantages of simplicity and of a higher yield.

SUMMARY OF THE INVENTION

Accordingly, an object of the invention is a process for preparing polyalkyl perylene, characterized in that it consists in subjecting the corresponding polyalkyl 1,1'-dinaphthalene derivative to a cyclodehydrogenation by a alkali metal.

A further object of the invention are polysubstituted perylenes comprised of a perylene ring system, tetrasubstituted with alkyl radicals.

Yet a further object of the invention are organic materials exhibiting an electron spin resonance spectrum, said materials comprising in their composition a tetrasubstituted polyalkyl perylene.

BRIEF DESCRIPTION OF THE DRAWINGS

The invention will be better understood and other advantages will become apparent from the following non limiting decription, taken in conjunction with the accompanying drawings, of which:

FIG. 1 illustrates the chemical reaction, which enables 3,4,9,10-tetramethyl perylene to be obtained;

FIG. 2 illustrates the chemical reaction, which enables 2,5,8,11-tetramethyl perylene to be obtained.

DESCRIPTION OF THE PREFERRED EMBODIMENTS

Until now, only a few alkyl perylenes have been synthetized. Such are the three monomethyl regioisomers of 1-(n-butyl)-perylene, of 1- and 2-ethyl perylene, and of 2,8-, 3,9- and 2,11-dimethyl perylenes. Higher substituted alkyl perylenes are rare, and only the 1,2,7,8-tetrahydrocyclopenta [cd; Im] perylene was synthetized, with a low yield (N. TANAKA, T. KASAI, Bulletin of the Chemical Society of Japan, 1981, Vol. 54, p. 3026).

In prior art, monosubstituted perylenes are obtained through electrophilic reactions (R. LAPOUYADE, J. PEREYRE and P. GARRIGUES, Comptes Rendus de l'Academie des Sciences de Paris, Vol. 303, p. 903, 1986). However, the regiospecific synthesis of di-substituted derivatives can only be achieved through a multi-step process, involving the synthesis of the perylene ring system per se (H. E. ZIEGER, J. E. ROSENKRANZ, Journal of Organic Chemistry, Vol. 29 p. 2469, 1964). Known syntheses of perylene per se are troublesome or involve numerous steps, and the yield is low (E. CLAR, Polycyclic Hydrocarbons, Vol. II, Acad. Press, 1964, p. 24). Their practice can involve reacting naphthalene, 1,1'-dinaphthalene or its 2,2'-dihydroxy derivative at high temperature. One can use a process of the Ullmann type (for example, using 1,8-diiodonaphthalenes) or photochemical extrusion reactions of tin-based derivatives prepared from the abovementioned diiodo compounds. Multi-step cyclization processes using as starting material other polyaromatic hydrocarbons, such as anthracene or phenanthrene, have also been described.

The possibility of preparing perylene from 1,1'-dinaphthalene through the action of metallic lithium has been known for a long time (H. GILMAN, C. G. BRANNEN, Journal of the American Chemical Society, 1949, Vol. 71, p. 657). However, this processs has been restricted to the preparation of the basic perylene.

According to the invention, the general reaction scheme comprises the following steps. An alkali metal powder, suspended in an inert solvent, is introduced into an apparatus with a reflux condenser and heated while stirring vigorously under an inert atmosphere. 1,1'-dinaphthalene, substituted with an alkyl radical selected according to the desired polyalkyl perylene, is added. The mixture is heated under reflux. A change in colour of the reaction mixture is noted after some time, corresponding probably to the formation of intermediate radical anions. The mixture is allowed to cool down to room temperature, and oxygen is then blown into the flask containing the mixture. A discolouration is noted. The excess alkali metal is removed by filtration and washed with a small amount of the reaction solvent. The solvent is then evaporated under vacuum and a brown material is collected, which is subjected to chromatography. The substituted perylenes thus obtained are recrystallized with xylene.

To illustrate the general reaction scheme, several Examples of preparation of polyalkyl perylenes, which are not intended to be limiting, will be described.

Also, the alkaline metal used in these Examples will be lithium.

EXAMPLE 1

Synthesis of 3,4,9,10-tetramethyl perylene

Firstly, one has to prepare the corresponding substituted 1,1'-dinaphthalene, namely the 4,4',5,5'-tetramethyl-1,1'-dinaphthalene. This compound is obtained with a 32% yield from 1,8-dimethyl naphthalene—which can be obtained from the MERCK Company—through oxidative coupling with lead tetraacetate, using a known procedure (A. McKILLOP, A. G. TURRELL, D. W. YOUNG, E. C. TAYLOR, Journal of the American Chemical Society 1980, Vol. 102, p. 6504).

The synthesis is then continued in accordance with the general reaction scheme described above, using the chemical reaction illustrated in FIG. 1. A suspension of lithium powder is prepared in an inert solvent, for example in tetrahydrofurane (THF). The proportion may be the following: 1.5 g, i.e. 220 millimoles, of lithium per 170 ml of THF. Argon can be used as the neutral atmosphere in the refluxing apparatus. 3 millimoles of solid 4,4',5,5'-tetramethyl 1,1'-dinaphthalene are then added. The refluxing is continued at 65° C. during 5 hours, which corresponds to the disappearing of the original 1,1'-dinaphthalene. The reaction mixture turns blue after the first three hours of heating. After cooling and injection of oxygen, the colour of the mixture turns yellow. The excess lithium is removed and the solvent is evaporated. A chromatography is performed on silicagel, using dichloromethane as the eluant. The 3,4,9,10-tetramethyl perylene is obtained by recrystallization with xylene. The yield in this preparation is 40%.

EXAMPLE 2

Synthesis of 2,5,8,11-tetramethyl perylene

The first step consists in preparing the corresponding substituted 1,1'-dinaphthalene, namely the 4,4'-dibromo-3,3',6,6'-tetramethyl-1,1'-dinaphthalene. This product is obtained with a 32% yield from 1-bromo-2,7-dimethylnaphthalene (J. WOLINSKA-MOCYDLARZ, P. CANONNE, L. C. LEICHT, Synthesis, 1974, p. 566) by coupling with thallium III trifluoroacetate (A. McKILLOP, A. G. TURRELL, D. W. YOUNG; E. C. TAYLOR, Journal of the American Chemical Society, 1980, Vol. 102, p. 6504).

The synthesis is then continued according to the general reaction scheme described above, using the chemical reaction illustrated in FIG. 2. As in the case of Example 1, the mixture containing the suspended lithium powder can be prepared with THF as solvent, in the same proportion. Argon can be used as the neutral atmosphere in the refluxing apparatus. 3 millimoles of solid 4,4'-dibromo-3,3',6,6'-tetramethyl-1,1'-dinaphthalene are added. The mixture is refluxed at 65° C. for 5 hours until the original 1,1'-dinaphthalene has disappeared. The reaction mixture turns dark purple after the first three hours of heating. After cooling and injection of oxygen, the mixture turns red. The excess lithium is removed and the solvent is evaporated. A chromatography on silicagel is carried out, using a mixture of toluene and cyclohexane (respectively, 15 and 85%, in volume) as eluant. The 2,5,8,11-tetramethyl perylene is obtained by recrystallization with xylene. The yield in this preparation is 36%.

In Examples 1 and 2, use was made of the so-called flash chromatography technique (W. CLARKSTILL, M. KAHN, A. MITRA, Journal of Organic Chemistry, 1978, Vol. 43, p. 2923).

The process of the invention, is not only easy to carry out, but also has the advantage of a higher yield (40 and 36% in, respectively, Examples 1 and 2) as compared to the prior art processes.

Other perylenes, tetra-substituted by an alkyl radical, than those described in Examples 1 and 2, can be prepared without departing from the invention. For this purpose, it suffices to prepare the corresponding polyalkyl 1,1'-dinaphthalene derivative using the above-mentioned prior art procedure.

The new molecules prepared according to the process of the invention can be used for preparing materials having remarkable electron spin resonance properties. These materials can be obtained by the well known electrocrystallization technique. For example, the anodic oxidation of 3,4,9,10-tetramethyl perylene (TMP) can be carried out at $-30°$ C. with a $3.10^{-5}$M solution in dichloromethane (anhydrous, and in the absence of oxygen) in the presence of tetrabutylammonium hexafluorophosphate ($5.10^{-4}$M). The current used during this operation amounts to a few $\mu$A. The isolated material corresponds to the formula:

$$[(TMP)_2PF_6, nCH_2Cl_2] \text{ with } 0 < n \leq 2$$

The dichloromethane $CH_2Cl_2$ can be got rid of by a prolonged heating under vacuum at above 80° C.

This material has an ESR line width of 16 milligauss at room temperature. It has the advantage of being stable up to above 80° C., and of being stable in air.

The anion $PF^-_6$ can be replaced by $As^-_6$ using tetrabutylammonium hexafluoroarsenate as the starting material to obtain a material having analogous ESR properties.

The new materials obtained exhibit a remarkable electron spin resonance spectrum and since they are stable at room temperature, they can advantageously replace fluoranthene based materials in the realization of gaussmeters or magnetometers.

We claim:

1. A polyalkyl perylene compound which has the formula:

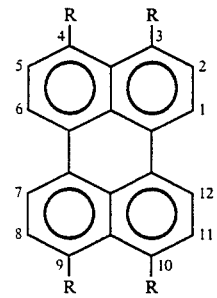

wherein R is methyl.

* * * * *